United States Patent
Guo et al.

(10) Patent No.: US 11,504,549 B2
(45) Date of Patent: Nov. 22, 2022

(54) SUPPORT ARM AND RADIOTHERAPY EQUIPMENT

(71) Applicants: SHENZHEN OUR NEW MEDICAL TECHNOLOGIES DEVELOPMENT CO., LTD., Shenzhen (CN); OUR UNITED CORPORATION, Xi'an (CN); OUR INNOBEAM MEDICAL CO., LTD, Beijing (CN)

(72) Inventors: Zhao Guo, Xi'an (CN); Yueming Yang, Xi'an (CN)

(73) Assignees: Shenzhen Our New Medical Technologies Development Co., Ltd., Shenzhen (CN); Our United Corporation, Xi'an (CN); Our Innobeam Medical Co., Ltd, Beijing (CN)

(*) Notice: Subject to any disclaimer, the term of this patent is extended or adjusted under 35 U.S.C. 154(b) by 59 days.

(21) Appl. No.: 17/059,194

(22) PCT Filed: May 24, 2019

(86) PCT No.: PCT/CN2019/088319
§ 371 (c)(1),
(2) Date: Nov. 25, 2020

(87) PCT Pub. No.: WO2019/223778
PCT Pub. Date: Nov. 28, 2019

(65) Prior Publication Data
US 2021/0196982 A1   Jul. 1, 2021

(30) Foreign Application Priority Data

May 25, 2018 (CN) .......................... 201820797673.8

(51) Int. Cl.
*A61N 5/10* (2006.01)

(52) U.S. Cl.
CPC .... *A61N 5/1049* (2013.01); *A61N 2005/1054* (2013.01); *A61N 2005/1063* (2013.01)

(58) Field of Classification Search
CPC .......... A61N 5/00; A61N 5/10; A61N 5/1049; A61N 2005/1054; A61N 2005/1063
See application file for complete search history.

(56) References Cited

U.S. PATENT DOCUMENTS

| 10,022,564 B2 | 7/2018 | Thieme et al. |
| 2003/0086526 A1 | 5/2003 | Clark et al. |
| 2009/0283682 A1 | 11/2009 | Star-Lack et al. |
| 2016/0074673 A1 | 3/2016 | Allen et al. |

FOREIGN PATENT DOCUMENTS

| CN | 105413067 A | 3/2016 |
| CN | 107041997 A | 8/2017 |

OTHER PUBLICATIONS

International search report and Written Opinion received in International application No. PCT/CN2019/088319 dated Jul. 25, 2019.

*Primary Examiner* — Jurie Yun
(74) *Attorney, Agent, or Firm* — Knobbe, Martens, Olson & Bear, LLP

(57) ABSTRACT

Provided is a support arm, including a guide assembly configured to be connected to a gantry of a radiotherapy equipment; a support bracket movably connected to the guide assembly and configured to support a detector; and a drive assembly connected to the support bracket and configured to drive the support bracket to move on the guide assembly.

19 Claims, 4 Drawing Sheets

SUPPORT ARM AND RADIOTHERAPY EQUIPMENT

The present application is a national phase application of International Application No. PCT/CN2019/088319, filed on May 24, 2019, which claims priority to Chinese Patent Application No. 201820797673.8, filed on May 25, 2018 and entitled "SUPPORT ARM AND RADIOTHERAPY EQUIPMENT OF ELECTRONIC PORTAL IMAGING DEVICE," each of which is incorporated herein by reference in its entirety.

TECHNICAL FIELD

The present disclosure relates to the field of medical instruments, and in particular relates to a support arm for an electronic portal imaging device and a radiotherapy equipment.

BACKGROUND

Generally, an electronic portal imaging device (EPID) is configured to verify a shape of a radiation field formed by a radiation beam emitted from a treatment head in a radiotherapy equipment and a radiation dose of the radiation field.

For example, before treatment of a patient by using the radiotherapy equipment, it is necessary to formulate a treatment plan, which includes at least one radiation field and a radiation dose corresponding to each radiation field. After the treatment plan is formulated, the radiation beam emitted from the treatment head in the radiotherapy equipment is controlled to be directly projected onto the EPID, and then the EPID detects whether the shape of the radiation field formed by the radiation beam is consistent with that of the corresponding radiation field in the treatment plan and makes a response. During the process of treating the patient by the radiotherapy equipment, the radiation beam emitted from the treatment head is controlled to pass through a target area of the patient and is then projected onto the EPID. The EPID detects whether the radiation dose of the radiation beam is consistent with the corresponding radiation dose in the treatment plan and makes a response. In this way, the EPID can ensure accurate treatment for the patient with the radiotherapy equipment.

SUMMARY

The present disclosure provides a support arm and a radiotherapy equipment. The technical solutions are as follows:

In a first aspect, a support arm is provided. The support arm includes: a guide assembly configured to be connected to a gantry of a radiotherapy equipment; a support bracket movably connected to the guide assembly and configured to support a detector; and a drive assembly connected to the support bracket and configured to drive the support bracket to move on the guide assembly.

Optionally, the drive assembly includes a drive motor and an actuator fixedly connected to the support bracket; wherein the drive motor is configured to drive the actuator to move, such that the support bracket is driven to move on the guide assembly.

Optionally, the actuator includes a drive gear; the guide assembly includes a rack in mesh with the drive gear; and the drive motor is connected to the drive gear, and the drive motor is configured to drive the drive gear to move along an extending direction of the rack, such that the support bracket is driven to move on the rack.

Optionally, the drive motor includes a motor output shaft and a brake, wherein the motor output shaft is fixedly connected to the drive gear, and the brake is configured to lock the motor output shaft after the support bracket is moved, such that the support bracket is fixed on the guide assembly.

Optionally, the support arm further includes a position detection assembly fixedly connected to the support bracket; wherein the position detection assembly includes a detection gear and a position encoder, wherein the detection gear is in mesh with the rack, the position encoder is connected to the detection gear, and the position encoder is configured to detect current position information of the support bracket relative to the rack based on rotation information of the detection gear.

Optionally, the drive assembly further includes a motor encoder, the motor encoder and the drive motor are coaxially disposed, and the motor encoder is electrically connected to the position encoder.

Optionally, the support arm also includes a connector fixedly connected to the support bracket, wherein the drive motor and the drive gear are both fixedly connected to the connector, and the detection gear and the position encoder are both fixedly connected to the connector.

Optionally, the connector is a plate-shaped structure, wherein the connector has two support surfaces opposite each other, the drive motor and the drive gear are respectively on the two support surfaces, and the detection gear and the position encoder are respectively on the two support surfaces.

Optionally, the detection gear and the drive gear are on one same support surface of the connector, and the drive motor and the position encoder are on another same support surface of the connector.

Optionally, the support arm further includes at least two position sensors fixedly connected to the guide assembly; wherein each of the position sensors is configured to determine position information of the support bracket relative to the rack.

Optionally, the actuator includes a drive nut; and the guide assembly includes a screw rod movably connected to the drive nut; wherein the drive motor is connected to the screw rod, and the drive motor is configured to drive the drive nut to move along an extending direction of the screw rod, such that the support bracket is driven to move on the screw rod.

Optionally, the guide assembly further includes a slide rail fixedly connected to the rack.

Optionally, the rack is an arc-shaped rack and the slide rail is an arc-shaped slide rail; wherein a circle center of the rack is in coincidence with a circle center of the slide rail.

Optionally, the support arm further includes a support flange, the support flange is configured to be fixedly connected to the gantry, and the guide assembly is fixedly connected to the support flange.

Optionally, the support flange is a ring-shaped flange, and the guide assembly includes an arc-shaped slide rail, and a circle center of the guide assembly is in coincidence with a circle center of the support flange.

Optionally, the support arm further includes a drag chain connected to the guide assembly, and a cable electrically connected to the detector is disposed in the drag chain.

In a second aspect, a radiotherapy equipment is provided. The radiotherapy equipment includes: a gantry, a support arm connected to the gantry, and the detector supported by a support bracket in the support arm, wherein the support arm includes the support arm according to the first aspect.

Optionally, the radiotherapy equipment further includes a treatment head connected to the gantry; wherein the drive assembly is configured to drive the support bracket to move on the guide assembly, such that the detector is opposite to the treatment head when the detector is in an operating state; and the drive assembly is further configured to drive the support bracket to move on the guide assembly, such that the detector is not opposite to the treatment head when the detector is in a non-operating state.

Optionally, the drive assembly includes: a drive motor, a drive gear connected to the support bracket, and a rack connected to the guide assembly; wherein an extending direction of the rack is the same as an extending direction of the guide assembly, and the drive gear is in mesh with the rack; the drive motor is configured to drive the drive gear to move along the extending direction of the rack and thereof to drive the support bracket to move on the guide assembly, such that the detector is opposite to the treatment head when the detector is in an operating state; and the drive motor is further configured to drive the drive gear to move along the extending direction of the rack and thereof to drive the support bracket to move on the guide assembly, such that the detector is not opposite to the treatment head when the detector is in a non-operating state.

Optionally, the drive motor includes a motor output shaft fixedly connected to the drive gear and a brake; wherein the brake is configured to lock the motor output shaft if the detector is opposite to the treatment head, such that the support bracket is fixed on the guide assembly when the detector is in an operating state; and the brake is further configured to lock the motor output shaft if the detector is not opposite to the treatment head, such that the support bracket is fixed on the guide assembly when the detector is in a non-operating state.

BRIEF DESCRIPTION OF THE DRAWINGS

In order to describe the technical solutions in the embodiments of the present disclosure more clearly, the following briefly introduces the accompanying drawings required for describing the embodiments. Apparently, the accompanying drawings as described below show merely some embodiments of the present disclosure, and a person of ordinary skill in the art may also derive other drawings from these accompanying drawings without creative efforts.

DETAILED DESCRIPTION

For clearer descriptions of the present disclosure, the embodiments of the present disclosure are further described in detail in combination with the accompanying drawings.

Figure 1:
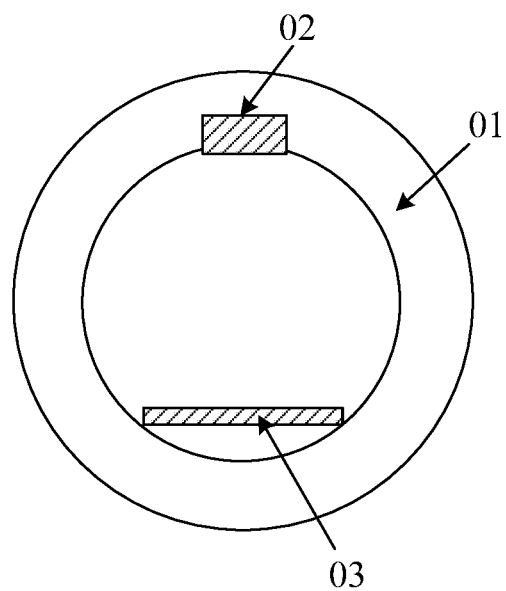
FIG. 1 is a schematic structural diagram of a radiotherapy equipment according to related arts.

Referring to FIG. 1, FIG. 1 is a schematic structural diagram of a radiotherapy equipment according to related arts. The radiotherapy equipment may include a gantry 01, a treatment head 02 and an EPID 03. The treatment head 02 and the EPID 03 are both connected to the gantry 01, and both rotate with the rotation of the gantry 01. The EPID 03 is always directly opposite to the treatment head 01. In fact, not treatments of all patients need to be verified by the EPID. However, in the current radiotherapy equipment, the EPID is always directly opposite to the treatment head. If the treatment of a patient does not need to be verified by the EPID 03 and the patent is treated in the radiotherapy equipment, the radiation beam emitted from the treatment head 01 may still be projected onto the EPID 03, resulting in a shorter service life of the EPID 03.

Figure 2:
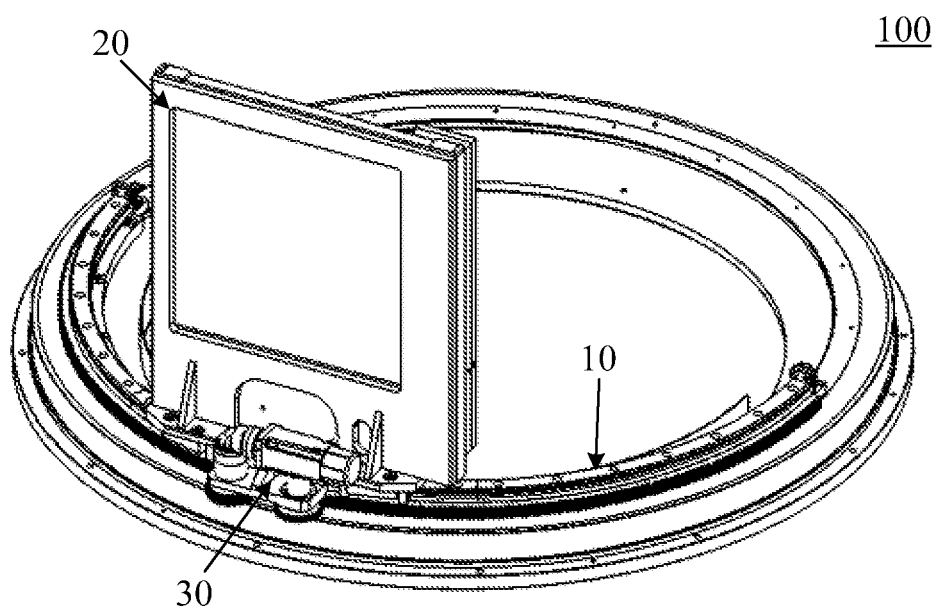
FIG. 2 is a schematic structural diagram of a support arm for an EPID according to an embodiment of the present disclosure.

Referring to FIG. 2. FIG. 2 is a schematic structural diagram of a support arm for the EPID according to an embodiment of the present disclosure. The support arm 100 for the EPID may include: a guide assembly 10, a support bracket 20 and a drive assembly 30.

The guide assembly 10 is configured to be connected to the gantry of a radiotherapy equipment. The support bracket 20 is configured to support the EPID (not marked in FIG. 2), and the support bracket 20 is movably connected to the guide assembly 10.

The drive assembly 30 is connected to the support bracket 20, and the drive assembly 30 is configured to drive the support bracket 20 to move on the guide assembly 10.

Figure 3:
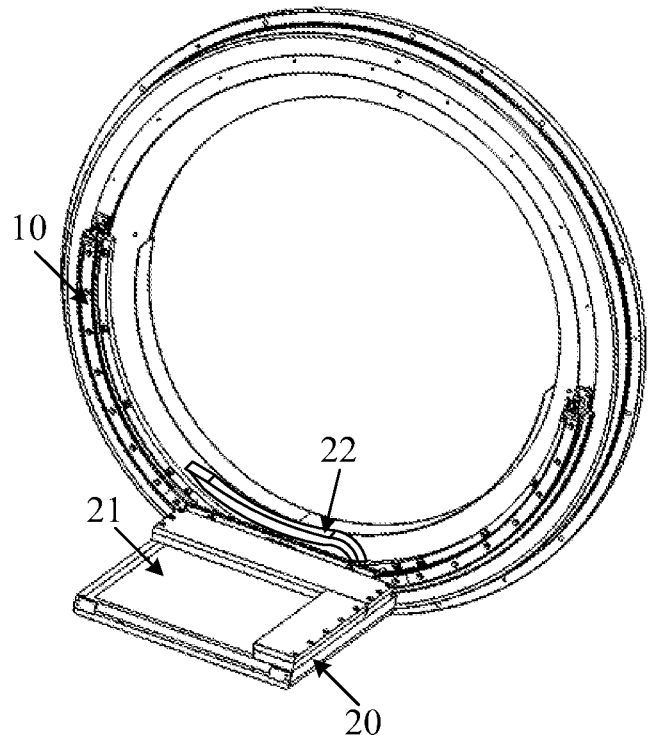
FIG. 3 is a schematic structural diagram of another side of the support arm for the EPID as shown in FIG. 2.

For a clearer view of a position of the EPID on the support bracket 20, reference may be made to FIG. 3. FIG. 3 is a schematic structural diagram of another side of the support arm for the EPID as shown in FIG. 2. The EPID 21 may be disposed on a support surface of the support bracket 20. The support arm 100 for the EPID may further include a drag chain 22 connected to the guide assembly 10. A cable electrically connected to the EPID 21 is disposed in the drag chain 22. The cable electrically connected to the EPID 21 can be protected by the drag chain 22, thereby avoiding the damage to the cable electrically connected to the EPID 21 when the support bracket 20 moves on the guide assembly 10.

Figure 4:
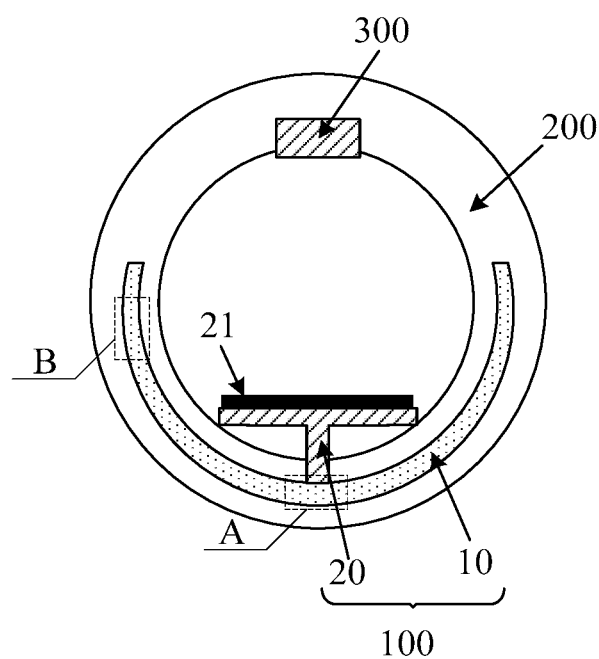
FIG. 4 is a schematic structural diagram of a radiotherapy equipment according to an embodiment of the present disclosure.

In the embodiment of the present disclosure, when the support arm 100 for the EPID is assembled with the gantry of the radiotherapy equipment, reference may be made to FIG. 4. FIG. 4 is a schematic structural diagram of the radiotherapy equipment according to an embodiment of the present disclosure. The guide assembly 10 may be connected to the gantry 200, thereby realizing the assembly of the support arm 100 for the EPID and the gantry 200. If the EPID is required for verification during treatment of the radiotherapy equipment, the drive assembly (not marked in FIG. 4) may drive the support bracket 20 to move on the guide assembly 10. It is assumed that when the drive assembly drives the support bracket 20 to move to the position A in the guide assembly 10, the EPID 21 on the support bracket 20 is directly opposite to the treatment head 300 in the radiotherapy equipment. In this case, the radiation beam emitted by the treatment head 300 can be projected onto the EPID 21. If the EPID is not required for verification during treatment of the radiotherapy equipment, the drive assembly may drive the support bracket 20 to move on the guide assembly 10. It is assumed that when the drive assembly drives the support bracket 20 to move to the position B in the guide assembly 10, the EPID 21 on the support bracket 20 is not opposite to the treatment head 300 in the radiotherapy equipment. In this case, the radiation beam emitted by the treatment head 300 may not be projected onto the EPID 21.

In summary, the support arm for the EPID according to the present disclosure includes the guide assembly, the support bracket, and the drive assembly. The guide assembly is configured to be connected to the gantry of the radiotherapy equipment, and the support bracket is configured to support the EPID. The support bracket is movably connected to the guide assembly, and the drive assembly is connected to the support bracket. The drive assembly is configured to drive the support bracket to move on the guide assembly. When the radiotherapy equipment is configured for treatment without a verification by EPID, the support bracket is driven by the drive assembly to move on the guide assembly, such that the EPID on the support bracket is not opposite to the treatment head in the radiotherapy equipment. In this way, the radiation beam emitted from the treatment head may not be projected onto the EPID, thereby effectively prolonging the service life of the EPID.

In the embodiment of the present disclosure, the drive assembly 30 may include a drive motor and an actuator fixedly connected to the support bracket. The drive motor is configured to drive the actuator to move, such that the support bracket 20 is driven to move on the guide assembly 10. It should be noted that the actuator in the drive assembly 30 has a plurality of structures, embodiments of the present disclosure take the following two schematic implementations as examples for description.

Figure 5:
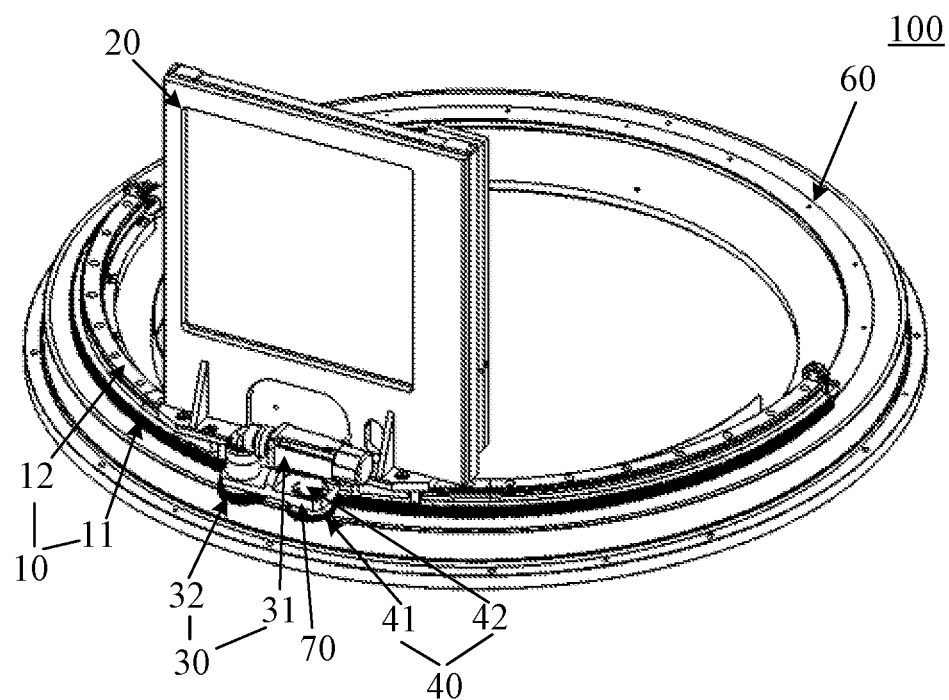
FIG. 5 is a schematic structural diagram of another support arm for the EPID according to an embodiment of the present disclosure.

In a first schematic embodiment, referring to FIG. 5, FIG. 5 is a schematic structural diagram of another support arm for the EPID according to an embodiment of the present disclosure. The actuator in the drive assembly 30 may include a drive gear 32. The drive gear 32 may be connected to the drive motor 31. The guide assembly 10 may include a rack 11 in mesh with the drive gear 32. It should be noted that the support arm 100 for the EPID may further include a connector 70 fixedly connected to the support bracket 20. The drive motor 31 and the drive gear 32 in the drive assembly 30 may be both fixedly connected to the connector 70, and the drive assembly 30 can be fixedly connected to the support bracket 20 by the connector 70.

The drive motor 31 is configured to drive the drive gear 32 to rotate, such that the drive gear 32 is driven to move along an extending direction of the rack 11, such that the support bracket 20 can move on the rack 11. In the embodiment of the present disclosure, the guide assembly 10 may further include a slide rail 12 fixedly connected to the rack 11. For example, the slide rail 12 may be an arc-shaped slide rail, and the rack 11 may be an arc-shaped rack. A circle center of the slide rail 12 needs to be in coincidence with a circle center of the rack 11, such that it is ensured that the extending direction of the rack 11 is the same as the extending direction of the slide rail 32. It should be noted that the embodiment of the present disclosure takes a fact that the shapes of the slide rail and the rack are arc-shape as the examples for schematic illustration. In some other embodiments, the shapes of the slide rail and the rack may also be linear or circular, which is not limited in the embodiment of the present disclosure.

Optionally, as shown in FIG. 5, the support arm 100 for the EPID may further include a support flange 60 configured to be fixedly connected to the gantry. The slide rail 12 in the guide assembly 10 may be fixedly connected to the support flange 60. Illustratively, the gantry may be a roller-type gantry or a drum-type gantry, etc. The support flange 60 may be fixedly connected to an end surface of the gantry to form a single-arm support structure. In this case, the support flange 60 may be a ring-shaped flange. If the slide rail 12 is an arc-shaped slide rail, a circle center of the support flange 60 may be in coincidence with the circle center of the slide rail 12. A radius of the slide rail 12 is matched with a radius of the support flange 60, such that the slide rail 12 is more easily disposed on the support flange 60. A diameter of the support flange 60 also needs to be matched with a diameter of the gantry of the radiotherapy equipment to be assembled, which effectively reduces the assembly difficulty of the support flange 60 and the gantry.

Figure 6:
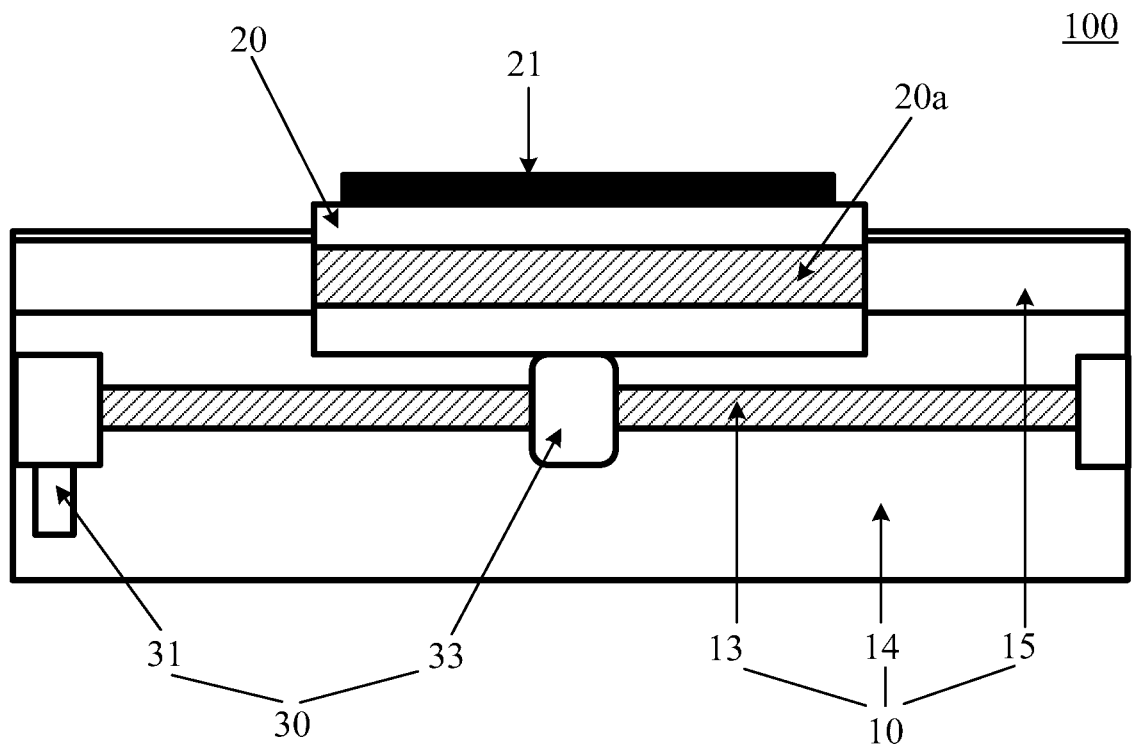
FIG. 6 is a schematic structural diagram of still another support arm for the EPID according to an embodiment of the present disclosure.

In a second schematic embodiment, reference may be made to FIG. 6. FIG. 6 is a schematic structural diagram of still another support arm for the EPID according to an embodiment of the present disclosure. The actuator in the drive assembly 30 may include a drive nut 33. The guide assembly 10 may include a screw rod 13 movably connected to the drive nut 33. The screw rod 13 may be connected to the drive motor 31 in the drive assembly 30. The drive motor 31 is configured to drive the screw rod 13 to rotate, such that the drive nut 33 is driven to move along the extending direction of the screw rod 13. Therefore, the support bracket 20 can move on the screw rod 13.

In the embodiment of the present disclosure, the support bracket 20 may include a movable slide rail 20a. For example, the movable slide rail 20a may be a convex structure, and the convex structure may be disposed on two opposite side surfaces of the support bracket 20. The two side surfaces are both perpendicular to the support surface for supporting the EPID 21. The guide assembly 10 may further include a support 14 and a static slide rail 15 disposed in the support 14. For example, the static slide rail 15 may be a groove structure matched with the shape of the movable slide rail 20a, such that the static slide rail 15 may be movably connected to the movable slide rail 20a. An extending direction of the movable slide rail 20a and an extending direction of the static slide rail 15 are both parallel to the extending direction of the screw rod 13. The screw rod 13 in the guide assembly 10 may be fixedly connected to the support 14 in the support bracket 20. The support 14 is configured to be fixedly connected to the gantry. Through the support 14, the assembly of the support arm 100 for the EPID and the gantry can be realized.

Illustratively, when the drive motor 31 in the drive assembly 30 drives the screw rod 13 to rotate, the drive nut 33 can move on the screw rod 13, and the movable slide rail 20a in the support bracket 20 can move in the static slide rail 15, such that the support bracket 20 can move along the extending direction of the screw rod 13. Due to the cooperation of the movable slide rail 20a and the static slide rail 15, the stability of the support bracket 20 during movement is improved.

The following embodiment takes the structure of the drive assembly in the first schematic implementation as an example for further illustration.

As shown in FIG. 5, the drive motor 31 may include a motor output shaft (not marked in FIG. 5) and a brake (not marked in FIG. 5). The motor output shaft is fixedly connected to the drive gear 32, and the drive motor 31 may drive the motor output shaft to rotate, thereby driving the drive gear 32 to rotate. The brake is configured to lock the motor output shaft after the support bracket 20 is moved, such that the drive gear 32 stops rotating, and further there is no relative movement between the drive gear 32 and the rack 11. The support bracket may be fixed on the guide assembly through the brake.

Illustratively, when the drive motor 31 drives the drive gear 32 to rotate such that the support bracket 20 moves to a preset designated position in the guide assembly 10, the brake in the drive motor 31 locks the motor output shaft, such that the support bracket 20 is fixed at the preset designated position. The preset designated position may include a first designated position (the first position is the position A in FIG. 4) and a second designated position (the second position is the position B in FIG. 4). When the support bracket 20 moves to the first designated position, the radiation beam emitted from the treatment head in the radiotherapy equipment may be projected onto the EPID after the brake in the drive motor 31 locks the motor output shaft. When the support bracket 20 moves to the second designated position, the radiation beam emitted from the treatment head in the radiotherapy equipment may not be projected onto the EPID after the brake in the drive motor 31 locks the motor output shaft.

In the embodiment of the present disclosure, in order to accurately fix the support bracket 20 at the preset designated position by the brake in the drive motor 31, it is necessary to accurately determine whether the support bracket 20 moves to the designated position. Whether the support bracket 20 has moved to the designated position may be determined in a plurality of ways. Embodiments of the present disclosure takes the following two ways as examples for schematic illustration.

Figure 7:
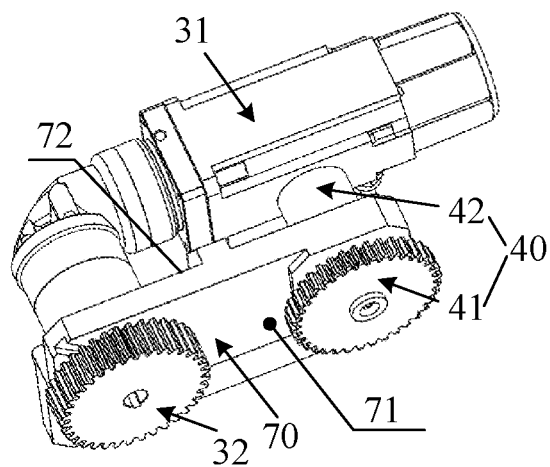
FIG. 7 is a schematic structural diagram of a position detection assembly according to an embodiment of the present disclosure.

In the first way, the support arm for the EPID may further include a position detection assembly fixedly connected to the support bracket. Referring to FIG. 5 or FIG. 7, FIG. 7 is a schematic structural diagram of the position detection assembly according to an embodiment of the present disclosure. The position detection assembly 40 may include a detection gear 41 and a position encoder 42. The detection gear 41 is in mesh with the rack 11, and the detection gear 41 is connected to the position encoder 42. For example, the position encoder 42 is provided with a transmission shaft therein, and a fixed connection between the position encoder 42 and the detection gear 41 may be realized by the transmission shaft.

Optionally, the detection gear 41 and the position encoder 42 in the position detection assembly 40 are both fixedly connected to the connector 70. The connector 70 can not only realize the fixed connection between the drive assembly 30 and the support bracket 20, but also realize the fixed connection between the position detection assembly 40 and the support bracket 20.

Illustratively, the connector 70 may have a plate-shaped structure, and the connector has two support surfaces opposite each other. The drive motor 31 and the drive gear 32 may be respectively disposed on the two support surfaces. The detection gear 41 and the position encoder 42 may also be disposed on the two support surfaces respectively. The detection gear 41 and the drive gear 32 are disposed on the same support surface of the connector 70, and the drive motor 31 and the position encoder 42 are disposed on the same support surface of the connector. For example, the two support surfaces may be a support surface 71 and a support surface 72 respectively. The detection gear 41 and the drive gear 32 may be both disposed on the support surface 71, and the drive motor 31 and the position encoder 42 may be both disposed on the support surface 72.

In the embodiment of the present disclosure, the position encoder 42 is configured to detect current position information of the support bracket 20 relative to the rack 11 based on rotation information of the detection gear 41. Illustratively, the position encoder 42 may determine teeth number information of the detection gear 41 moving relative to the rack 11, and may detect the current position information of the support bracket 20 relative to the rack 11 based on the teeth number information. In this way, the position encoder 42 may determine whether the support bracket 20 has moved to the preset designated position according to the detected current position information of the support bracket 20. It should be noted that the position encoder 42 may be in a plurality of types. For example, the position encoder may be an incremental encoder, an absolute encoder, and a photoelectric encoder, which is not limited in the embodiment of the present disclosure.

In order to accurately move the support bracket 20 to the designated position, the drive assembly 30 may further include a motor encoder (not marked in FIG. 5 and FIG. 7), and the motor encoder and the drive motor 31 are coaxially disposed. The motor encoder is fixedly connected to the drive gear 32 by the motor output shaft in the drive motor, and the motor encoder is electrically connected to the position encoder 42. The motor encoder stores target position information indicating that the support bracket 20 needs to be fixed on the guide assembly 10. The motor encoder is configured to receive the current position information detected by the position encoder 42 and determine a drive duration of the drive motor 31 based on the target position information and the current position information. Illustratively, the motor encoder may receive the current position information of the support bracket 20 relative to the guide assembly 10 sent by the position encoder 42 in real time, and compare the current position information with the stored target position information to determine the drive duration of the drive motor 31 in real time, such that the support bracket 20 can be fixed at the preset designated position after being driven by the drive motor 31.

In another optional embodiment, the drive assembly may further include a drive controller. Both the drive motor and the position encoder are electrically connected to the drive controller. The drive controller stores the target position information indicating that the support bracket needs to be fixed on the guide assembly therein. The drive controller is configured to receive the current position information detected by the position encoder, determine a drive duration of the drive motor based on the target position information and the current position information, and control the drive motor according to the drive duration, such that the drive motor can accurately fix the support bracket at the preset designated position.

Figure 8:
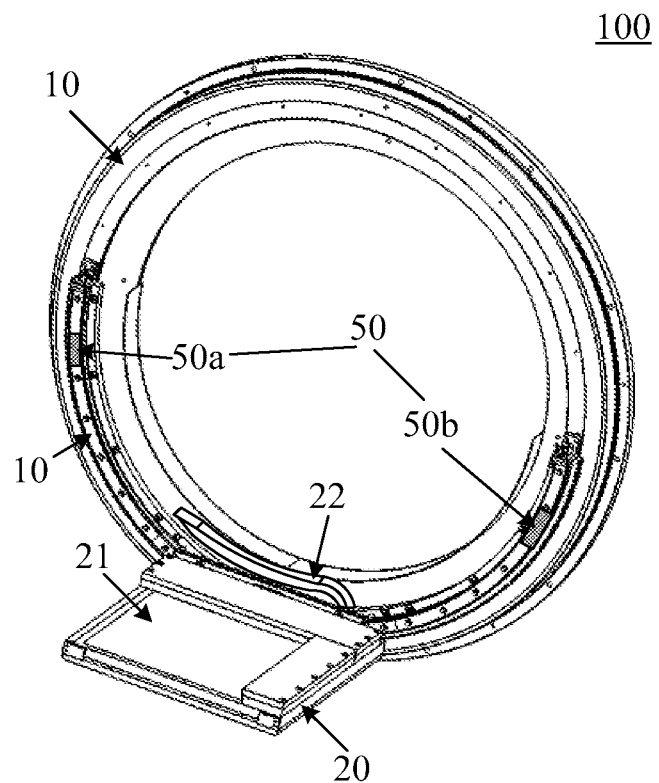
FIG. 8 is a schematic structural diagram of yet another support arm for the EPID according to an embodiment of the present disclosure.

In the second way, referring to FIG. 8, FIG. 8 is a schematic structural diagram of yet another support arm for the EPID according to an embodiment of the present disclosure. The support arm 100 for the EPID may also include at least two position sensors 50 fixedly connected to the guide assembly 10. Each position sensor 50 is configured to determine the position of the support bracket 20 relative to the rack (not marked in FIG. 8). Illustratively, the at least two position sensors 50 may be respectively disposed at preset designated positions in the guide assembly 10. For example, the position sensor 50a may be disposed at a first designated position (which may be the position A shown in FIG. 4), and the position sensor 50b may be disposed at a second designated position (which may be the position B in FIG. 4). During the process of driving the support bracket 20 to move on the guide assembly 10 by the drive motor, when the position sensor 50a detects that the support bracket 20 moves to the first designated position, the brake in the drive motor locks the motor output shaft, such that the radiation beam emitted from the treatment head in the radiotherapy equipment may be projected onto the EPID 21. When the position sensor 50b detects that the support bracket 20 moves to the second designated position, the brake in the drive motor locks the motor output shaft, and the radiation beam emitted from the treatment head in the radiotherapy equipment may not be projected onto the EPID 21. In the embodiment of the present disclosure, the position sensor may be a photoelectric sensor.

In summary, the support arm for the EPID according to the present disclosure includes the guide assembly, the support bracket, and the drive assembly. The guide assembly is configured to be connected to the gantry of the radiotherapy equipment, and the support bracket is configured to support the EPID. The support bracket is movably connected to the guide assembly, and the drive assembly is connected to the support bracket. The drive assembly is configured to drive the support bracket to move on the guide assembly. When the radiotherapy equipment is used for treatment without a verification by the EPID, the support bracket is driven by the drive assembly to move on the guide assembly, such that the EPID on the support bracket is not opposite to the treatment head in the radiotherapy equipment. In this way, the radiation beam emitted from the treatment head may not be projected onto the EPID, thereby effectively prolonging the service life of the EPID.

Embodiments of the present disclosure further provide a radiotherapy equipment, which may include a gantry, a support arm for an EPID connected to the gantry, and the EPID supported by a support bracket in the support arm for the EPID. The support arm for the EPID includes the support arm 100 for the EPID as shown in FIG. 2, FIG. 5, FIG. 6, or FIG. 8.

Optionally, the radiotherapy equipment may further include a treatment head connected to the gantry. The drive assembly 30 in the support arm 100 for the EPID is configured to drive the support bracket 20 to move on the guide assembly 10, such that the EPID is opposite to the treatment head when the EPID is in an operating state. The drive assembly 30 is also configured to drive the support bracket 20 to move on the guide assembly 10, such that the EPID is not opposite to the treatment head when the EPID is in a non-operating state.

Illustratively, the structure of the radiotherapy equipment may refer to FIG. 4. If the EPID is required for verification during treatment of the radiotherapy equipment, the drive assembly 30 may drive the support bracket 20 to move on the guide assembly 10. It is assumed that when the drive assembly 30 drives the support bracket 20 to move to the position A in the guide assembly 10, the EPID 21 on the support bracket 20 is directly opposite to the treatment head 300 in the radiotherapy equipment. In this case, the radiation beam emitted from the treatment head 300 can be projected onto the EPID 21. If the EPID is not required for verification during treatment of the radiotherapy equipment, the drive assembly 30 may drive the support bracket 20 to move on the guide assembly 10. It is assumed that when the drive assembly 30 drives the support bracket 20 to move to the position B in the guide assembly 10, the EPID 21 on the support bracket 20 is not opposite to the treatment head 300 in the radiotherapy equipment. In this case, the radiation beam emitted from the treatment head 300 may not be projected onto the EPID 21.

Optionally, the support arm 100 for the EPID in the radiotherapy equipment includes the support arm 100 for the EPID as shown in FIG. 5. The drive motor 31 in the drive assembly 30 is configured to drive the drive gear 32 to move along the extending direction of the rack 11 and thereof drive the support bracket 20 to move on the guide assembly 10, such that the EPID 21 is opposite to the treatment head when the EPID 21 is in the operating state. The drive motor 31 is also configured to drive the driving gear 32 to move along the extending direction of the rack 11 and thereof drive the support bracket 20 to move on the guide assembly 10, such that the EPID 21 is not opposite to the treatment head when the EPID 21 is in the non-operating state.

Optionally, the drive motor 21 may include a motor output shaft and a brake. The motor output shaft is fixedly connected to the drive gear. The brake is configured to lock the motor output shaft if the EPID 21 is opposite to the treatment head, such that the support bracket 20 is fixed on the guide assembly when the EPID 21 is in the operating state. In this case, the support bracket 20 is located at the position A in FIG. 4. The brake is also configured to lock the motor output shaft if the EPID 21 is not opposite to the treatment head, such that the support bracket is fixed on the guide assembly when the EPID 21 is in the non-operating state. In this case, the support bracket 20 is located at the position B in FIG. 4.

For the description, the present disclosure takes an electronic portal imaging device (EPID) as an example to describe the support arm. More specifically, when the radiation beam from the treatment head is in Mv-level, the EPID includes an Mv flat panel detector, which can receive the radiation beam of Mv-level. The level of the detector is consistent with the level of the radiation beam to be received.

In addition, the support arm provided by the present disclosure is applicable to other detectors, for example, a detector that may receive radiation beams of Mv and Kv levels at the same time. The embodiment of the present disclosure does not limit the shape of the detector. For example, the detector may be a flat-panel detector, or an arc-shaped detector. The embodiments of the present disclosure also do not limit the number of detectors. For example, the detector may include detectors of different levels, such as Mv detectors and Kv detectors, or multiple detectors of the same level, such as multiple Mv detectors. When in an operating state, the detector is moved to be opposite to the treatment head by the support arm, and when in a non-operating state, the detector is moved to be not opposite to the treatment head by the support arm, thereby prolonging the service life of the detector.

Described above are merely preferred embodiments of the present disclosure, and is not intended to limit the present disclosure. Within the spirit and principles of the present disclosure, any modifications, equivalent substitutions, improvements, and the like fall within the protection scope of the present disclosure.

What is claimed is:

1. A support arm, comprising:
    a guide assembly configured to be connected to a gantry of a radiotherapy equipment;
    a support bracket movably connected to the guide assembly and configured to support a detector; and
    a drive assembly connected to the support bracket and configured to drive the support bracket to move on the guide assembly, the support arm further comprising a drag chain connected to the guide assembly, wherein a cable electrically connected to the detector is disposed in the drag chain.

2. The support arm according to claim 1, wherein the drive assembly comprises a drive motor and an actuator fixedly connected to the support bracket; wherein
the drive motor is configured to drive the actuator to move, such that the support bracket is driven to move on the guide assembly.

3. The support arm according to claim 2, wherein the actuator comprises a drive gear, and the guide assembly comprises a rack in mesh with the drive gear; wherein
the drive motor is connected to the drive gear, and the drive motor is configured to drive the drive gear to move along an extending direction of the rack, such that the support bracket is driven to move on the rack.

4. The support arm according to claim 3, wherein the drive motor comprises a motor output shaft and a brake; wherein
the motor output shaft is fixedly connected to the drive gear, and the brake is configured to lock the motor output shaft after the support bracket is moved, such that the support bracket is fixed on the guide assembly.

5. The support arm according to claim 3, further comprising: a position detection assembly fixedly connected to the support bracket, wherein
the position detection assembly comprises a detection gear and a position encoder, wherein the detection gear is in mesh with the rack, the position encoder is connected to the detection gear, and the position encoder is configured to detect current position information of the support bracket relative to the rack based on rotation information of the detection gear.

6. The support arm according to claim 5, wherein the drive assembly further comprises a motor encoder; wherein
the motor encoder and the drive motor are coaxially disposed, and the motor encoder is electrically connected to the position encoder.

7. The support arm according to claim 5, further comprising a connector fixedly connected to the support bracket, wherein
the drive motor and the drive gear are both fixedly connected to the connector, and the detection gear and the position encoder are both fixedly connected to the connector.

8. The support arm according to claim 7, wherein the connector is a plate-shaped structure; wherein
the connector comprises two support surfaces opposite each other, the drive motor and the drive gear are respectively on the two support surfaces, and the detection gear and the position encoder are respectively on the two support surfaces.

9. The support arm according to claim 8, wherein
the detection gear and the drive gear are on one same support surface of the connector, and
the drive motor and the position encoder are on another same support surface of the connector.

10. The support arm according to claim 3, further comprising: at least two position sensors fixedly connected to the guide assembly, wherein
each of the position sensors is configured to determine position information of the support bracket relative to the rack.

11. The support arm according to claim 3, wherein the guide assembly further comprises a slide rail fixedly connected to the rack.

12. The support arm according to claim 11, wherein the rack is an arc-shaped rack and the slide rail is an arc-shaped slide rail; wherein
a circle center of the rack is in coincidence with a circle center of the slide rail.

13. The support arm according to claim 2, wherein the actuator comprises a drive nut, and the guide assembly comprises a screw rod movably connected to the drive nut; wherein
the drive motor is connected to the screw rod, and the drive motor is configured to drive the drive nut to move along an extending direction of the screw rod, such that the support bracket is driven to move on the screw rod.

14. The support arm according to claim 1, further comprising a support flange, wherein
the support flange is configured to be fixedly connected to the gantry, and the guide assembly is fixedly connected to the support flange.

15. The support arm according to claim 14, wherein the support flange is a ring-shaped flange, and the guide assembly comprises an arc-shaped slide rail; wherein
a circle center of the guide assembly is in coincidence with a circle center of the support flange.

16. A radiotherapy equipment, comprising:
a gantry, a support arm connected to the gantry, and a detector supported by a support bracket in the support arm, wherein the support arm comprises:
a guide assembly configured to be connected to the gantry of the radiotherapy equipment;
the support bracket movably connected to the guide assembly and configured to support the detector; and
a drive assembly connected to the support bracket and configured to drive the support bracket to move on the guide assembly,
the support arm further comprising a drag chain connected to the guide assembly, wherein a cable electrically connected to the detector is disposed in the drag chain.

17. The radiotherapy equipment according to claim 16, further comprising a treatment head connected to the gantry; wherein:
the drive assembly is configured to drive the support bracket to move on the guide assembly, such that the detector is opposite to the treatment head when the detector is in an operating state; and
the drive assembly is further configured to drive the support bracket to move on the guide assembly, such that the detector is not opposite to the treatment head when the detector is in a non-operating state.

18. The radiotherapy equipment according to claim 17, wherein the drive assembly comprises: a drive motor and a drive gear connected to the support bracket; and
a rack is connected to the guide assembly, wherein an extending direction of the rack is same as an extending direction of the guide assembly, and the drive gear is in mesh with the rack;
wherein:
the drive motor is configured to drive the drive gear to move along the extending direction of the rack and thereof to drive the support bracket to move on the guide assembly, such that the detector is opposite to the treatment head when the detector is in an operating state; and
the drive motor is further configured to drive the drive gear to move along the extending direction of the rack and thereof to drive the support bracket to move on the guide assembly, such that the detector is not opposite to the treatment head when the detector is in a non-operating state.

19. The radiotherapy equipment according to claim 18, wherein the drive motor comprises a motor output shaft fixedly connected to the drive gear and a brake; wherein:
  the brake is configured to lock the motor output shaft if the detector is opposite to the treatment head, such that the support bracket is fixed on the guide assembly when the detector is in an operating state; and
  the brake is further configured to lock the motor output shaft if the detector is not opposite to the treatment head, such that the support bracket is fixed on the guide assembly when the detector is in a non-operating state.

* * * * *